United States Patent [19]

Roberts et al.

[11] 3,994,910
[45] Nov. 30, 1976

[54] DERIVATIVES OF 1,2-DIPHENYL-3,5-DIOXO-4-N-BUTYL-PYRAZOLIDINE AND PROCESS FOR MAKING SAME

[75] Inventors: David J. Roberts; Jacinto Moragues Mauri, both of Barcelona, Spain

[73] Assignee: Antonia Gallardo, S.A., Barcelona, Spain

[22] Filed: Mar. 6, 1974

[21] Appl. No.: 448,748

[30] Foreign Application Priority Data
Mar. 30, 1973 France .............................. 73.11666

[52] U.S. Cl. ...................... 260/306.7 T; 260/295 Q; 260/295 L; 424/263; 424/270
[51] Int. Cl.² ............... C07D 231/34; C07D 213/73
[58] Field of Search ............................. 260/306.7 T

[56] References Cited
UNITED STATES PATENTS
3,177,118   4/1965   Baetz............................ 260/306.7 T
FOREIGN PATENTS OR APPLICATIONS
2,181,666   12/1973   France OTHER PUBLICATIONS
Gallardo Carrera, Chem. Abstracts, 79:105251s, (1973).
Kazumasa et al., Chem. Abstracts, 65:14073d, (1966).
The Merck Index, Eighth Ed., Merck & Co., Rahway, N.J., 1968, p. 815.

Primary Examiner—Raymond V. Rush
Assistant Examiner—Mark L. Berch
Attorney, Agent, or Firm—Morgan, Finnegan, Pine, Foley & Lee

[57] ABSTRACT

The present invention concerns novel therapeutic compounds having the formula:

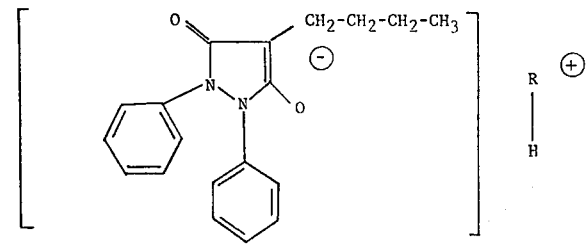

wherein R is a basic compound comprising 2-amino-4-methyl-pyridine or 2-amino-2-thiazoline, and methods of making this compound.

1 Claim, No Drawings

DERIVATIVES OF 1,2-DIPHENYL-3,5-DIOXO-4-N-BUTYL-PYRAZOLIDINE AND PROCESS FOR MAKING SAME

BACKGROUND OF THE INVENTION

Since its discovery almost a quarter of a century ago, phenylbutazone (4-n-butyl-1,2-diphenyl-3,5-pyrazolidinedione) has dominated the field of non-steroid anti-inflammatory drugs despite the fact that it has several serious toxic effects of which ulcerogenesis and fluid retention are probably the most frequent.

The most probable reason for the continued success of phenylbutazone is that none of the numerous modifications of its structure nor the even more numerous attempts to design novel structures with anti-inflammatory activity have resulted in a truly successful separation of desired pharmacological activity and undesired toxicity.

SUMMARY OF THE INVENTION

This invention relates to a process for preparing derivatives of 1,2-diphenyl-3,5-dioxo-4-n-butyl-pyrazolidine having the formula:

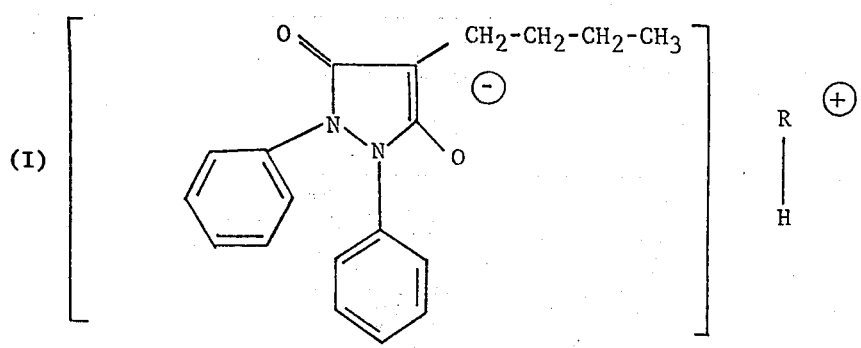

in which R is represented by a basic compound namely: either 2-amino-4-methyl-pyridine or 2-amino-2-thiazoline, having the respective formulae:

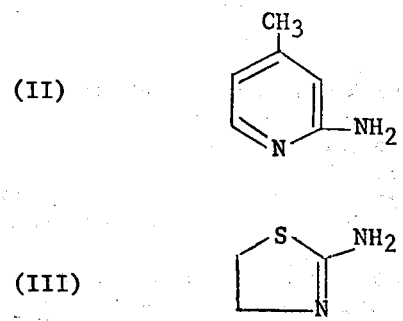

It has been found that the compounds of Formula I are a clear improvement over phenylbutazone in that they have increased therapeutic activities but reduced or decreased toxicity.

As will be more fully discussed hereinafter, the therapeutic compounds of the present invention have a number of additional advantages over phenylbutazone. For example, smaller doses of the new therapeutic compounds as compared with phenylbutazone can be used with comparable and superior effectiveness. The therapeutic compounds of the present invention have fewer and less severe side effects.

In equimolar reaction with 1,2-diphenyl-3,5-dioxo-4-n-butyl-pyrazolidine, these compounds form stable crystalline combinations with an interesting therapeutic action as anti-inflammatories, analgesics and analeptics.

Pharmacological testing of these compounds led to results to be described hereinafter and reflected in the compound formed by the equimolar combination of 1,2-diphenyl-3,5-dioxo-4-n-butyl-pyrazolidine-2-amino-2-thiazoline, referred to hereinafter as LAS-11871. The equimolar combination of phenylbutazone salt with 2-amino-4-methylpyridine is hereinafter referred to as LAS 6671.

The doses of compounds referred to are in mg of salt and not in mg equivalents of phenylbutazone content (i.e. the comparison has been made on a weight for weight basis and not equimolar) since it was considered that this would be more demonstrative of the potential value of the compound. Equimolar comparisons can be made by taking into account the respective molecular weights of LAS 11871 (410.54) and phenylbutazone (308.4) from which it is evident that 100 mg of LAS 11871 contains the equivalent of 75 mg of phenylbutazone.

DETAILED DESCRIPTION OF THE INVENTION

The properties and advantages of the therapeutic compounds of the present invention will be discussed below as to some of their therapeutic activities, their toxicity effects and their chemical functions and synthesis.

PHARMACOLOGY

LAS 11871 and 6671 were compared in a preliminary screening test with phenylbutazone and a commercially available piperazine salt of phenylbutazone and they had definite advantages over each of these two products (see Table 1 below).

TABLE 1

This shows the effects of LAS-11871 in various screening tests as compared with phenylbutazone and a piperazine salt thereof.

| Compound | Desired Effects | | | Toxic Effects | |
|---|---|---|---|---|---|
|  | CE | AA | AP | UG | TX |
| LAS 11871 | ++ | +++ | +++ | + | + |
| LAS 6671 | ++ | + | ++ | + | + |
| Phenylbutazone | ++ | ++ | ++ | ++ | ++ |
| Piperazine salt of Phenylbutazone | + | + | + | + | + |

CE = Inhibition of carrageenin-induced oedema in rat's paw. AA = Inhibition of contortions induced by acetic acid in mice. AP = Inhibition of yeast-induced pyrexia in rats. UG = Intensity of ulceration produced in the rat stomach. TX = Acute toxicity in mice.

More detailed studies confirmed these preliminary results and clearly showed that LAS 11871, although more active as an analgesic and anti-inflammatory agent than phenylbutazone, produces fewer gastric lesions and is less toxic than phenylbutazone (see Tables 2, 3, 4, 5 and 6 below).

TABLE 2

This shows the effect of various doses of phenylbutazone and LAS 11871 on carrageenin-induced oedema in the rat's paw.

| Compound per os 1 h before carrageenin | | No. of animals | Volume of paw (ml) standard error | % Inhibition ± standard error |
|---|---|---|---|---|
| Control | | 46 | 0.9663 ± 0.0564 | 0.00 ± 5.80 |
| Phenylbutazone | 200 | 12 | 0.2458 ± 0.0454** | 74.60 ± 4.70 |
| | 100 | 18 | 0.3139 ± 0.0224** | 67.50 ± 2.30 |
| | 50 | 22 | 0.6886 ± 0.0699* | 28.70 ± 7.24 |
| | 25 | 22 | 0.6545 ± 0.0545** | |
| LAS 11871 | 200 | 11 | 0.1545 ± 0.0384** | 84.00 ± 3.97 |
| | 100 | 18 | 0.2667 ± 0.0428** | 72.40 ± 4.43 |
| | 50 | 22 | 0.6182 ± 0.0683* | 36.01 ± 7.06 |
| | 25 | 22 | 0.7864 ± 0.0632 | 18.60 ± 6.54 |

Volume of paws measured 3 hours after injection of carrageenin *P <0.05, >0.001; **P <0.001 for the differences from the control using Student's "t" test.

TABLE 3

Effects of various doses of phenylbutazone and LAS 11871 on granuloma induced in rats by implantation of cotton balls.

| mg/Kg/day of compound per os | | No. of granulomas (animals) | Weight of wet granuloma | Dry granuloma ± standard error (mg) | Percentage inhibition Wet granuloma | Dry granuloma |
|---|---|---|---|---|---|---|
| Control | | 40 (20) | 454.20 ± 11.74 | 77.34 ± 0.33 | 0.00 ± 2.60 | 0.00 ± 0.40 |
| Phenylbutazone | 200 | 20 (10) | 353.40 ± 13.14** | 49.96 ± 4.25** | 22.20 ± 2.80 | 35.40 ± 5.50 |
| | 100 | 20 (10) | 424.50 ± 13.47 | 71.23 ± 5.18 | 6.50 ± 2.90 | 7.90 ± 6.70 |
| | 50 | 20 (10) | 434.75 ± 18.36 | 83.94 ± 8.22 | 4.30 ± 4.10 | 8.50 ± 10.6 |
| LAS 11871 | 200 | 20 (10) | 361.21 ± 12.84** | 48.29 ± 1.98** | 20.50 ± 2.80 | 37.60 ± 2.50 |
| | 100 | 20 (10) | 369.69 ± 16.68** | 61.95 ± 4.74* | 18.60 ± 3.70 | 19.90 ± 6.10 |
| | 50 | 20 (10) | 388.59 ± 8.74** | 61.82 ± 3.16** | 14.40 ± 1.90 | 20.00 ± 4.10 |

*P <0.05, >0.001
**P <0.001 for the differences from the control using Student's "t" test.

The figures refer to the net weight of granuloma tissue obtained by subtracting the original weight of the cotton ball.
*P <0.05, >0.001; **P <0.001 for the differences from the control using Student's "t" test.

TABLE 4

Effect of various doses of phenylbutazone and LAS 11871 on contortions induced by acetic acid injected into the abdominal cavity of the mouse.

| mg/kg of compound per os 1 h before acetic acid injection | | No. of animals | No. of contortions ± standard error | % inhibition ± standard error |
|---|---|---|---|---|
| Control | | 20 | 81.65 ± 5.73 | 0.00 ± 7.02 |
| Phenylbutazone | 300 | 10 | 42.30 ± 6.75** | 48.20 ± 8.27 |
| | 100 | 10 | 47.30 ± 6.70* | 42.10 ± 8.20 |
| | 30 | 10 | 59.00 ± 6.51* | 27.70 ± 7.97 |
| LAS 11871 | 300 | 10 | 24.10 ± 3.74** | 70.50 ± 4.60 |
| | 100 | 10 | 36.90 ± 6.34** | 54.90 ± 7.76 |
| | 30 | 10 | 44.20 ± 6.03** | 45.90 ± 7.39 |

*P <0.05, >0.001
**P >0.001 for the differences from the control using Student's "t" test.

TABLE 5

Ulcerogenic activity of LAS 11871 on the stomach as compared with phenylbutazone

| mg/kg of compound per os | | No. of animals | ± standard error of ulcerogenic indices |
|---|---|---|---|
| Control | | 40 | 0.17 ± 0.07 |
| Phenylbutazone | 2×200 | 29 | 5.00 ± 0.56 |
| | 2×100 | 30 | 4.33 ± 0.47 |
| | 2× 50 | 30 | 0.73 ± 0.21 |
| LAS 11871 | 2×200 | 29 | 3.65 ± 0.56* |
| | 2×100 | 30 | 2.43 ± 0.41** |
| | 2× 50 | 29 | 0.59 ± 0.19 |

*P <0.1, >0.01
**P <0.01 for the differences between equivalent doses of phenylbutazone and LAS 11871 using Student's "t" test.

From Table 2 it is demonstrated that LAS 11871 is at least as active as phenylbutazone against inflammation and at doses of 50 mg/kg and above LAS 11871 was the more active compound.

Table 3 compares the activity of LAS 11871 and phenylbutazone against chronic inflammation. It is seen that although both products produced about the same degree of inhibition of granuloma tissue formation at high doses (200 mg/kg), at the lower dose levels (100 and 50 mg/kg) LAS 11871 continued to inhibit the granuloma tissue formation but phenylbutazone did not.

Table 4 demonstrates that LAS 11871 is more potent than phenylbutazone as an analgesic.

Although LAS 11871, in common with virtually all of the other non-steroid anti-inflammatory compounds, possesses a certain capacity to cause ulcerous lesions in the gastro-intestinal tract. However, as Table 5 illustrates, it is much less active in this respect than phenylbutazone.

TOXICITY

LD50 per os in the rat of LAS 11871

| Group | Dose | No. animals | No. deaths | % mortality |
|---|---|---|---|---|
| I | 1000 mg/kg | 10 | 1 | 10 |
| II | 1210 mg/kg | 12 | 3 | 25 |
| III | 1470 mg/kg | 10 | 5 | 50 |
| IV | 1780 mg/kg | 10 | 9 | 90 |
| V | 2150 mg/kg | 10 | 10 | 100 |

LD50 ≃ 1425 mg/kg (1250 – 1624)

LD50 per os in the rat of phenylbutazone

| Group | Dose | No. animals | No. deaths | % mortality |
|---|---|---|---|---|
| I | 464 mg/kg | 9 | 1 | 11 |
| II | 562 mg/kg | 10 | 4 | 40 |
| III | 681 mg/kg | 10 | 8 | 80 |
| IV | 825 mg/kg | 10 | 8 | 80 |
| V | 1000 mg/kg | 10 | 9 | 90 |
| VI | 1210 mg/kg | 10 | 10 | 100 |

LD50 = (530 – 725)

LD50 per os in the rat of 2-amino-thiazoline

| Group | Dose | No. animals | No. deaths | % mortality |
|---|---|---|---|---|
| I | 316 mg/kg | 10 | 2 | 20 |
| II | 383 mg/kg | 10 | 4 | 40 |
| III | 464 mg/kg | 10 | 6 | 60 |
| IV | 562 mg/kg | 10 | 7 | 70 |
| V | 681 mg/kg | 10 | 9 | 90 |
| VI | 825 mg/kg | 10 | 9 | 90 |

LD50 ≃ 430 mg/kg (358 – 516)

In general, the new therapeutic compounds can be used to treat the same disorders as phenylbutazone. As the above discussion illustrates, the therapeutic compounds of the present invention are less toxic and less ulcerogenic than phenylbutazone, and they have greater effectiveness in anti-inflammatory, analgesic, and antipyretic activity. These therapeutic compounds have been found effective in treating humans as well as animals. For example, LAS 11871 has been shown effective in the treatment of humans with reumatic diseases and LAS 11871 has been used to successfully treat polyarthritics at doses of 200 mg. two, or three times per day.

These new therapeutic compounds also have limited and reduced side effects. As noted earlier, they have no anti-diuretic effect and relatively low ulcerogenic potential. They are also relatively free of serious side effects on the central nervous system.

However, the compounds, much more than phenylbutazone, show marked inhibition of spontaneous motor activity. This activity is best described as a tranquilizing or muscle relaxant activity. Also, the compounds appear to have immunosuppressant activity.

PHARMACEUTICAL FORMULATIONS

LAS 11871 capsules

| | g |
|---|---|
| LAS 11871 | 0.200 |
| Colloidal silica | 0.005 |

LAS 11871 tablets

| | |
|---|---|
| LAS 11871 | 0.250 |
| Hydroxypropyl cellulose | 0.016 |
| Microcrystalline cellulose | 0.100 |
| Carboxymethyl starch | 0.012 |
| Colloidal silica | 0.003 |
| Magnesium stearate | 0.003 |

LAS 11871 suppositories

| | |
|---|---|
| LAS 11871 | 0.300 |
| Stearine composition | 1.240 |

PHARMACEUTICAL FORMULATIONS-continued

LAS 11871 suppositories

| | |
|---|---|
| LAS 11871 | 0.5000 |
| Ascorbyl palmitate | 0.0025 |
| Stearine composition | 1.9975 |

Dose: from 200 to 1,500 mg/day

CHEMISTRY AND SYNTHESIS

The reaction process for synthesising the therapeutic compounds of the present invention is carried into effect with the use of organic solvents such as methanol, ethanol, acetone, methyl ethyl acetone and dioxane in conditions which will be described in the following Examples.

EXAMPLE 1

Equimolar combination of
1,2-diphenyl-3,5-dioxo-4-n-butylpyrazolidine-2-amino-4-methyl-pyridine 30.8 g (0.1 mol) of 1,2-diphenyl-3,5-dioxo-4-n-butyl-pyrazolidine are introduced with agitation into a 500 cc flask and mixed with 150 ml of acetone until complete dissolution. 10.8 g (0.1 mol) of 2-amino-4-methylpyridine which have previously been dissolved in 100 cc of acetone are then added and the mixture is boiled for 30 minutes. It is filtered cold, and 39 g of a product having a melting point of 121°–2° C are crystallized out.

EXAMPLE 2

Equimolar combination of
1,2-diphenyl-3,5-dioxo-4-n-butylpyrazolidine-2-amino-2-thiazoline Working is performed under the same conditions as in Example 1 but using ethyl alcohol as the solvent. 2.04 g (0.02 mol) of 2-amino-2-thiazoline are heated in ethanol with 6.16 g (0.02 mol) of 1,2-diphenyl-3,5-dioxo-4-n-butylpyrazolidine for 30 minutes; after cooling, the crystals which form are collected. The substance has a melting point of 161°–2° C. The yield is 86 percent. The final product was a white crystalline powder virtually insoluble in ether, sparingly soluble in water and soluble in hot ethanol.

What is claimed is:

1. A therapeutic compound having the formula:

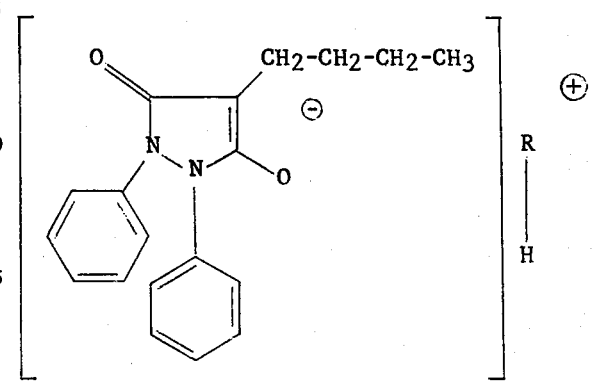

in which R is 2-amino-2-thiazoline having the formula:

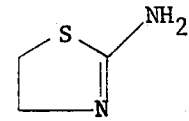

* * * * *

UNITED STATES PATENT AND TRADEMARK OFFICE
CERTIFICATE OF CORRECTION

PATENT NO. : 3,994,910

DATED : November 30, 1976

INVENTOR(S) : David J. Roberts, Jacinto Moragues Mauri

It is certified that error appears in the above-identified patent and that said Letters Patent are hereby corrected as shown below:

The name of the Assignee should read --Antonio Gallardo-- not "Antonia Gallardo".

Delete "Foreign Application Priority Data Mar. 30, 1973 France ... 73.11666".

Column 5, line 18, insert -- = -- between "LD50" and "1425"; line 26, "LD50 = (530-725)" should read --LD50 = 620(530-725)--; line 27, "2-amino-thiazoline" should be -- 2-amino-2-thiazoline --; line 33, insert -- = -- between "LD50" and "430"; line 43, "reumatic" should read -- rheumatic --.

Column 6, line 10, "synthesising" should read -- synthesizing --; line 12, replace "methyl ethyl acetone" with -- methyl ethyl ketone --.

Signed and Sealed this

Twentieth Day of December 1977

[SEAL]

Attest:

RUTH C. MASON
*Attesting Officer*

LUTRELLE F. PARKER
*Acting Commissioner of Patents and Trademarks*